(12) United States Patent
Wendland et al.

(10) Patent No.: US 11,103,650 B2
(45) Date of Patent: Aug. 31, 2021

(54) INJECTION DEVICE

(71) Applicant: Sanofi-Aventis Deutschland GmbH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 340 days.

(21) Appl. No.: 15/779,033

(22) PCT Filed: Nov. 21, 2016

(86) PCT No.: PCT/EP2016/078244
§ 371 (c)(1),
(2) Date: May 24, 2018

(87) PCT Pub. No.: WO2017/089256
PCT Pub. Date: Jun. 1, 2017

(65) Prior Publication Data
US 2018/0353703 A1   Dec. 13, 2018

(30) Foreign Application Priority Data

Nov. 27, 2015   (EP) .................................. 15196670

(51) Int. Cl.
*A61M 5/32* (2006.01)
*A61M 5/315* (2006.01)

(52) U.S. Cl.
CPC ...... *A61M 5/3204* (2013.01); *A61M 5/31546* (2013.01); *A61M 5/3202* (2013.01); *A61M 5/3243* (2013.01); *A61M 2005/3254* (2013.01); *A61M 2005/3267* (2013.01); *A61M 2205/583* (2013.01)

(58) Field of Classification Search
CPC .. A61M 5/3204; A61M 5/3202; A61M 5/321; A61M 5/24; A61M 5/2033;
(Continued)

(56) References Cited

U.S. PATENT DOCUMENTS 6,641,561 B1   11/2003   Hill et al.
7,654,987 B2   2/2010    Hommann et al.
(Continued)

FOREIGN PATENT DOCUMENTS

CN   101815549   8/2010
CN   101827622   9/2010
(Continued)

OTHER PUBLICATIONS

International Search Report and Written Opinion in International Application No. PCT/EP2016/078244, dated Feb. 22, 2017, 11 pages.
(Continued)

*Primary Examiner* — Kevin C Sirmons
*Assistant Examiner* — Antarius S Daniel
(74) *Attorney, Agent, or Firm* — Fish & Richardson P.C.

(57) ABSTRACT

An auto-injector device comprises a cap removal mechanism which comprises a retractable component which is slidably mounted within a housing of the device, and a cap-removal actuator to push the retractable component out of the housing to remove a cap from the device; a dispense mechanism which comprises a driving element to expel a medicament from the device; and a dispense button which activates the cap removal mechanism when pressed a first time, engages with the dispense mechanism when released, and activates the dispense mechanism when pressed a second time. The dispense mechanism comprises an engaging
(Continued)

element configured to engage with the dispense button when the dispense button has been pressed for a first time and released.

20 Claims, 12 Drawing Sheets

(58) Field of Classification Search
CPC .. A61M 5/20; A61M 5/3213; A61M 5/31545; A61M 5/31546; A61M 5/3243; A61M 5/31; A61M 2005/312; A61M 2005/3243; A61M 2005/3267; A61M 2005/2006; A61M 2005/2026; A61M 2005/2073; A61M 2205/583
See application file for complete search history.

(56) References Cited

U.S. PATENT DOCUMENTS

| | | | |
|---|---|---|---|
| 7,806,866 | B2 | 10/2010 | Hommann et al. |
| 8,460,245 | B2 * | 6/2013 | Guillermo ........... A61M 5/2033 604/135 |
| 2005/0261634 | A1 * | 11/2005 | Karlsson ............. A61M 5/2033 604/197 |
| 2011/0172640 | A1 * | 7/2011 | Cronenberg ...... A61M 5/31595 604/506 |
| 2012/0016296 | A1 | 1/2012 | Charles |
| 2014/0336589 | A1 | 11/2014 | Sund et al. |

FOREIGN PATENT DOCUMENTS

| | | |
|---|---|---|
| CN | 102186517 | 9/2011 |
| JP | 2005-074224 | 3/2005 |
| JP | 2006-507103 | 3/2006 |
| JP | 2015-504713 | 2/2015 |
| WO | WO 2009/019438 | 2/2009 |
| WO | WO 2009/019439 | 2/2009 |
| WO | WO 2010/033770 | 3/2010 |
| WO | WO 2013/092671 | 6/2013 |
| WO | WO 2014/131858 | 9/2014 |

OTHER PUBLICATIONS

International Preliminary Report on Patentability in International Application No. PCT/EP2016/078244, dated May 29, 2018, 7 pages.

* cited by examiner

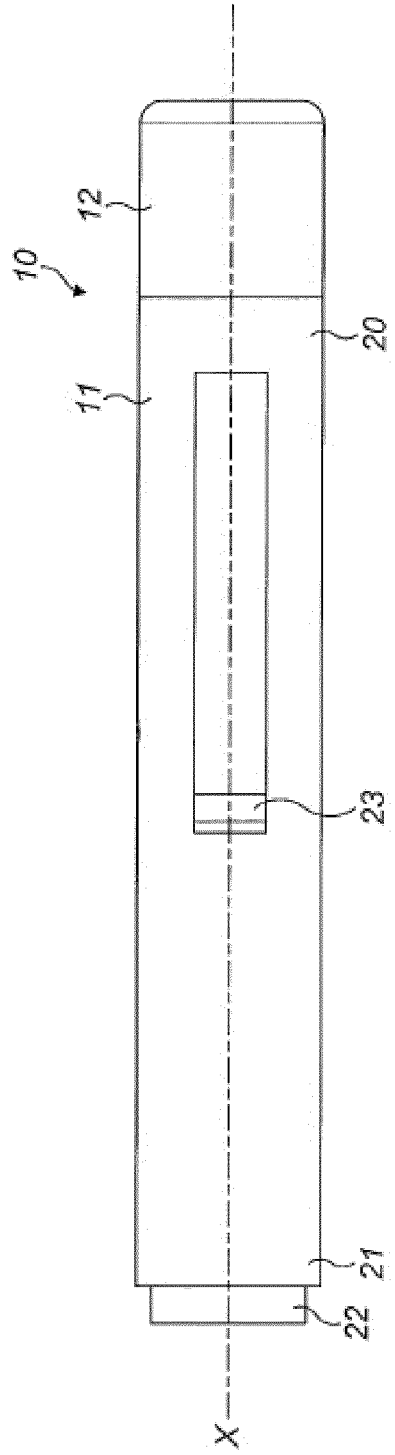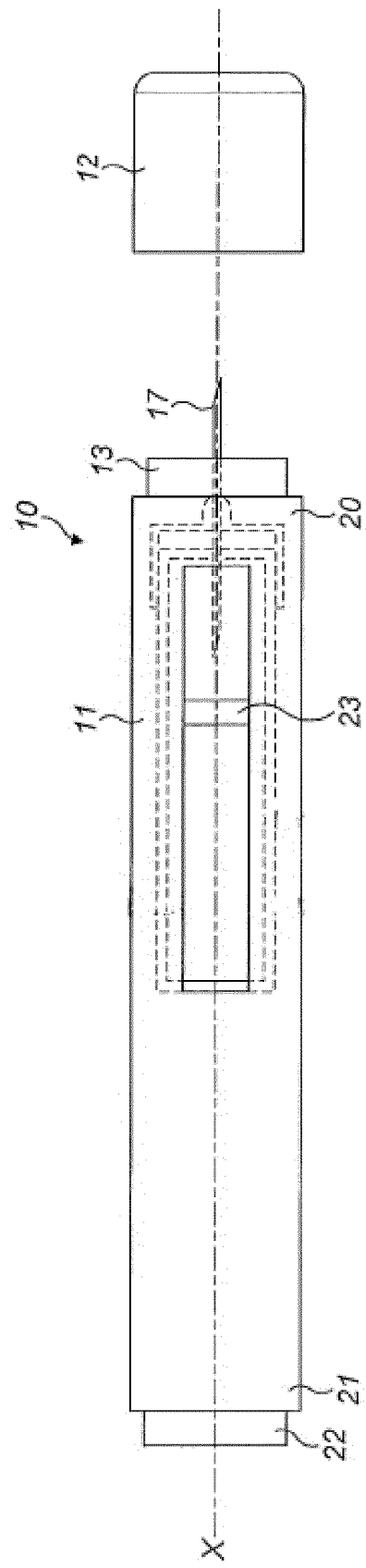
FIG. 1A
FIG. 1B

INJECTION DEVICE

CROSS REFERENCE TO RELATED APPLICATIONS

This application is a U.S. national stage application under 35 USC § 371 of International Patent Application No. PCT/EP2016/078244, filed on Nov. 21, 2016, which claims priority to European Patent Application No. 15196670.2, filed on Nov. 27, 2015, the entire contents of each of which are incorporated herein by reference.

TECHNICAL FIELD

The disclosure generally relates to an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It can be important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

According to an embodiment, an auto-injector device is provided, including a cap removal mechanism including a retractable component which is slidably mounted within a housing of the device, and a cap-removal actuator to push the retractable component out of the housing to remove a cap from the device; a dispense mechanism including a driving element to expel a medicament from the device; and a dispense button configured to activate the cap removal mechanism when pressed a first time, to engage with the dispense mechanism when released, and to activate the dispense mechanism when pressed a second time; wherein the dispense mechanism includes an engaging element configured to engage with the dispense button when the dispense button has been pressed for a first time and released.

The cap-removal actuator may include a cap-removal spring.

The dispense mechanism may include locking means configured to prevent activation of the dispense mechanism when locked.

The retractable component may unlock the locking means when the retractable element is pushed within the housing of the device.

The retractable component is in the form of a retractable sleeve.

The dispense button may include a first part and a second part.

The first part may couple with the second part when pressed a first time, and may retract with the second part when released.

The second part of the dispense button may be a different colour to the first part of the dispense button.

The second part of the dispense button when retracted by the first part may be arranged to engage with the engaging element of the dispense mechanism and may activate the dispense mechanism when the dispense button is pressed a second time.

The engaging element may be restrained in a disengaged position by the second part of the dispense button, and may move into an engaging position when the dispense button is released.

The engaging element may be arranged to engage with the second part in the engaging position.

The dispense button may include a spring element which is retained in a disengaged position by the cap removal mechanism and, when the cap removal mechanism is activated, moves into an engaging position.

The spring element may be arranged to engage with the dispense mechanism in the engaging position.

The device may include an active status marking which is uncovered when the dispense button is pressed for the first time and released.

The device may include a viewing window which is moved into alignment with the active status marking when the dispense button is pressed for a first time and released.

The device may include an initial status marking and a final status marking.

The viewing window may be aligned with the initial status marking before the dispense button is pressed, and aligned with the final status marking when the dispense button is pressed for a second time.

The device may include a medicament which is retained in a medicament reservoir and is arranged to be expelled from the medicament reservoir by the dispense mechanism.

According to another aspect, a method of operating an injection device is provided, including activating a cap removal mechanism in response to a received input; and activating a dispense mechanism in response to the input, if the input is received a second time.

The terms "drug" or "medicament" which are used interchangeably herein, mean a pharmaceutical formulation that includes at least one pharmaceutically active compound.

The term "drug delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems.

These and other aspects will be apparent from and elucidated with reference to the embodiments described hereinafter.

BRIEF DESCRIPTION OF THE DRAWINGS

Exemplary embodiments are described with reference to the accompanying drawings, in which:

FIG. 1A is a schematic side view of an injection device according to an exemplary embodiment, with a cap attached to a body of the injection device;

FIG. 1B is a schematic side view of the injection device of FIG. 1A, with the cap removed from the body;

DETAILED DESCRIPTION

Figure 2:
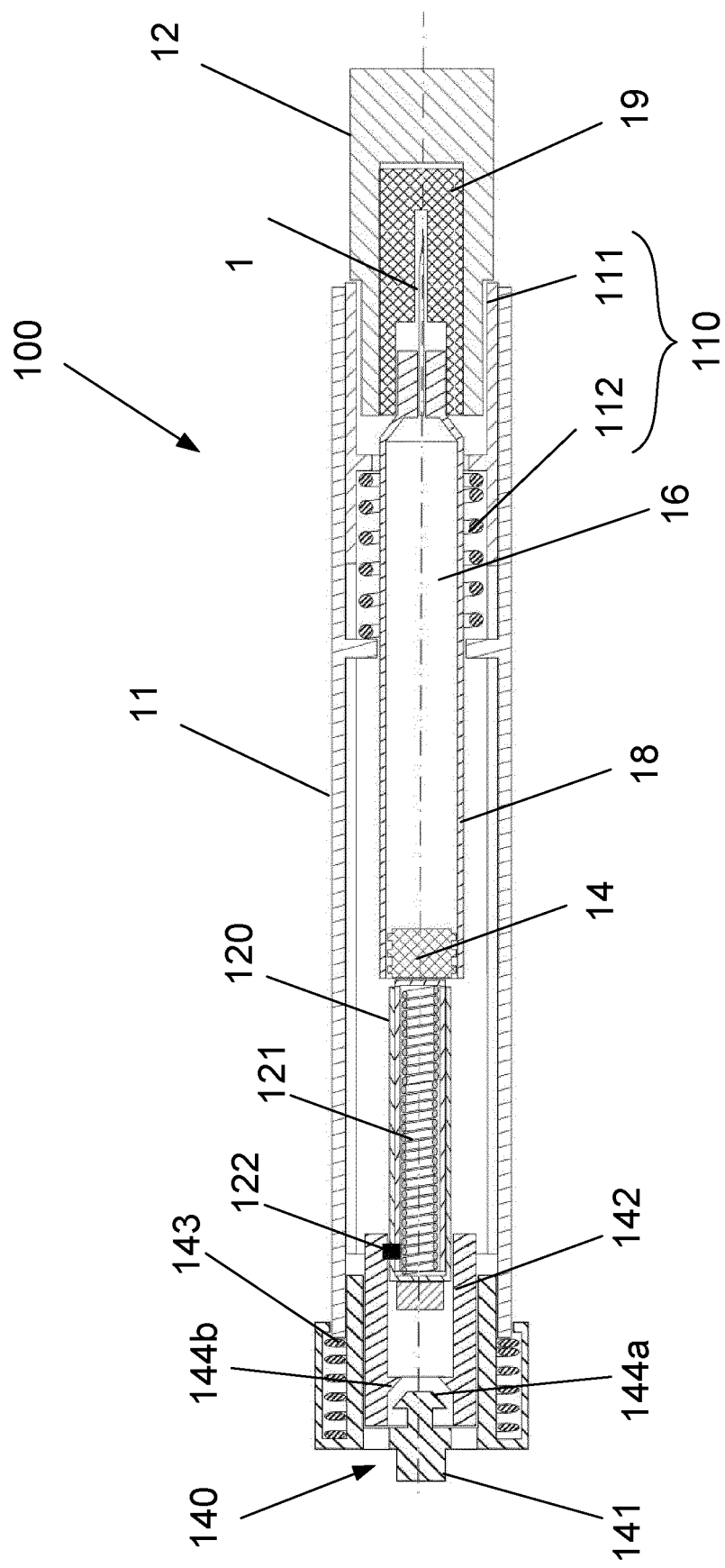
FIG. 2 is a schematic cross-sectional side view of the FIGS. 1A and 1B injection device according to an exemplary embodiment.

One or more embodiments provide an auto-injector device and a mechanism for activating the auto-injector device, which is configured also to remove the cap from the device.

A dispense button is provided on the device which is configured to activate a cap removal mechanism when pressed for a first time, and to activate the dispense mechanism when pressed for a second time. The auto-injector thus provided is safe to use, as the cap of the auto-injector is removed without the use of force by the user, and is also easy to use, as a single button can be used to prepare and activate the device. Other aspects also provide a visual indication of the device status, which improves usability.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

With reference to FIG. 2, an injection device 100 according to a first embodiment is shown. The injection device 100 comprises a housing 11, a syringe 18 containing liquid medicament 16, a cap 12, a cap removal mechanism 110, a dispense mechanism 120 and a dispense button 140.

The syringe 18 is a tubular container having an open proximal end which forms a medicament reservoir. A rubber stopper 14 is received in the open end of the syringe 18 to seal the container and retain the liquid medicament 16 within. A needle 17 extends from a distal end of the syringe 18 through an opening in a distal end of the housing 11. The needle 17 is covered by a needle shield 19 which is formed from rubber.

The dispense mechanism 120 is mechanically coupled to the syringe 18 and is configured to dispense the liquid medicament 16 out of the syringe 18 through the needle 17. A driving element 121, which is a coil compression spring, is disposed adjacent to a proximal end of the syringe 18 and is mechanically coupled to the rubber stopper 14. The coil compression spring is pre-stressed in order to expand and drive the rubber stopper 14 through the medicament reservoir when the dispense mechanism 120 is activated. The dispense mechanism 120 further comprises engaging means 122 to engage with the dispense button 140, such that the dispense mechanism 120 is activated when the dispense button 140 is pressed.

The cap 12 is provided to enclose the distal end of the housing 11 and to conceal the needle 17. The cap 12 comprises a cylindrical wall and an end wall. An inner diameter of the cap 12 is arranged to fit tightly over the needle shield 19. The outer surface of the cylindrical wall has a stepped profile, with the proximal end of the cap 12 having a smaller diameter than the distal end. With the cap 12 located on the injection device 100, an external surface of the cylindrical wall fits within the opening at the distal end of the housing 11 and abuts an internal surface within the opening, so that the cap 12 is retained therein.

To inject the liquid medicament 16, the cap 12 and needle shield 19 must be removed from the injection device 100 to uncover the needle 17. The cap removal mechanism 110 comprises a retractable sleeve 111 and a sleeve spring 112 for deploying the retractable sleeve 111. The retractable sleeve 111 is disposed within the opening at the distal end of the housing 11 and is slideably coupled to the housing 11 in order to move in and out of the distal end of the housing 11. The proximal end of the retractable sleeve 111 extends towards the proximal end of the housing 11. The sleeve spring 112 is mounted within the retractable sleeve 111, and is coupled between a reaction surface of the retractable sleeve 111 at a distal end of the sleeve spring 112 and a reaction surface of the housing 11 at a proximal end of the sleeve spring 112. The sleeve spring 112 is arranged to exert an axial force to push the retractable sleeve 111 out of the distal end of the housing 11.

The cap 12 is arranged to fit loosely within the retractable sleeve 111, with the proximal end of the cylindrical wall in abutment with an internal surface of the retractable sleeve 111. The distal end of the retractable sleeve 111 abuts the stepped profile of the cylindrical wall of the cap 12. When the cap removal mechanism 110 is activated the retractable sleeve 111 is driven axially in a distal direction by the sleeve spring 112, and exerts an axial force on the cap 12 to remove the cap 12 from the housing 11. The needle shield 19 is removed with the cap 12 by the cap removal mechanism 110.

Prior to the activation of the cap removal mechanism 110, the retractable sleeve 111 is in a retracted position and lies wholly within the opening at the distal end of the housing 11. The sleeve spring 112 is fully compressed when the retractable sleeve 111 is in the initial retracted position. The retractable sleeve 111 is retained in the retracted position by a trigger (not shown) which is released when the cap removal mechanism 110 is activated. When the cap removal mechanism 110 is activated the sleeve spring 112 drives the retractable sleeve 111 to a final position in which a proximal portion of the retractable sleeve 111 is retained within the housing 11, and a distal portion of the retractable sleeve 111 extends from the distal end of the housing 11. The retractable sleeve 111 in the final position extends beyond the needle 17, which is uncovered by the removal of the cap 12 and needle shield 19.

The dispense button 140 is configured to sequentially activate the cap removal mechanism 110 and the dispense mechanism 120. The dispense button 140 activates the cap removal mechanism 110 when pressed a first time and engages with the dispense mechanism 120 when released, such that the dispense mechanism 120 is activated when the dispense button 140 is pressed a second time.

The dispense button 140 is disposed within an opening at the proximal end of the housing 11 and comprises a first part 141, a second part 142 and a return spring 143. The first part 141 of the dispense button 140 comprises an inner portion and an outer portion which are fixed together and moveable slideably along the longitudinal axis with respect to the housing 11. The outer portion is disposed adjacent to the proximal end of the housing 11 and the return spring 143 is arranged between the proximal end of the housing 11 at the distal end of the return spring 143 and the outer portion of the first part 141 at the proximal end of the return spring 143. The return spring 143 exerts an axial force on the first part 141 in a proximal direction, so as to bias the first part 141 to an initial position.

The outer portion of the first part 141 is formed from two concentric cylindrical walls, with one wall disposed within the opening at the proximal end of the housing 11, and another wall positioned externally around the proximal end of the housing 11. The proximal ends of the two concentric cylinders are joined by an annular end portion, such that an internal space is enclosed by the cylinder walls, the end portion and the proximal end of the housing 11. The return spring 143 is disposed within the internal space of the outer portion, and exerts an axial force on the annular end portion to push the first part 141 of the dispense button 140 away from the housing 11.

The inner portion of the first part 141 is disposed centrally with respect to the opening at the proximal end of the house, and extends proximally beyond the outer portion of the first part 141. The distal end of the inner portion comprises a coupling element 144a for coupling with the second part 142 of the dispense button 140.

The second part 142 of the dispense button 140 is formed as a cylindrical tube disposed between the inner portion and the outer portion of the first part 141. A coupling element 144b disposed on an inner surface of the second part 142 is configured to couple with the first part 141, and a distal end of the second part 142 is arranged to engage with the engaging means 122 of the dispense mechanism 120. The second part 142 of the dispense button 140, in an initial state, is positioned forwards of the first part 141 and so does not protrude from the proximal end of the injection device 100, as shown in FIG. 2. The engaging means 122 is not initially engaged with the dispense mechanism 120 and the coupling element 144a of the first part 141 is spaced apart from the coupling element 144b of the second part 142 in the initial state.

When the dispense button 140 is pressed for the first time, the first part 141 of the dispense button 140 is moved axially towards the housing 11 and the second part 142 remains stationary with respect to the housing 11.

Figure 3:
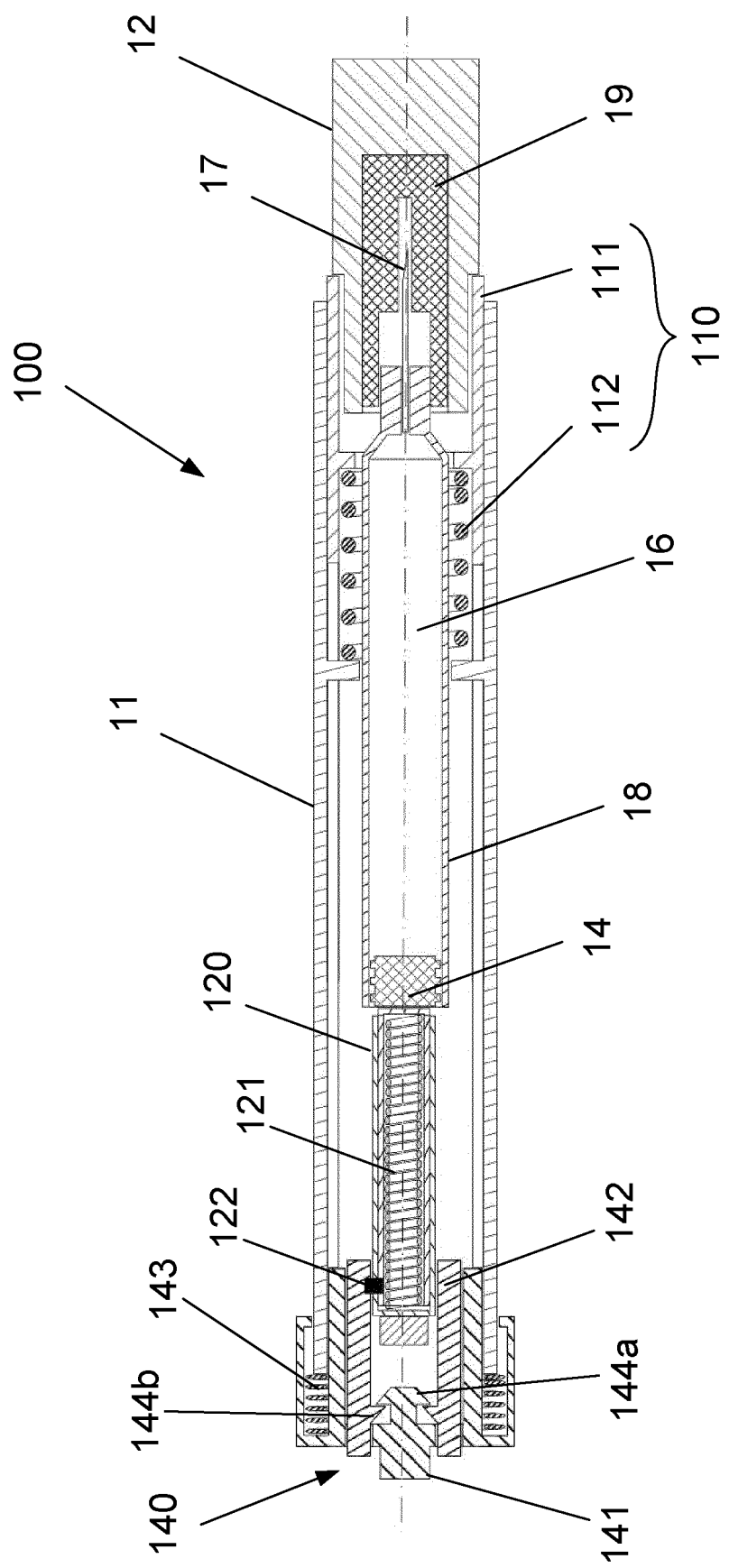
FIG. 3 is a schematic cross-sectional side view of the injection device of FIG. 2.

FIG. 3 shows the injection device 100 according to the first embodiment with the dispense button 140 in a second position, when pressed for the first time. In the second position, the first part 141 is pushed into the proximal end of the housing 11 and the return spring 143 is compressed. The coupling element 144a of the first part 141 and the coupling element 144b of the second part 142 are brought into contact and couple together, such that the second part 142 of the dispense button 140 is fixed to the first part 141. The coupling elements 144a,144b of the first part 141 and second part 142 are formed by interlocking retainer clips.

In the second position, the distal end of the outer portion of the first part 141, which is within the housing 11, is pushed against the proximal end of the retractable sleeve 111. The axial force on the retractable sleeve 111 releases the trigger of the cap removal mechanism 110, which releases the sleeve spring 112 to expand and push the retractable sleeve 111 and the cap 12 in a distal direction. The cap removal mechanism 110 is activated by dispense button 140 when pressed for the first time.

Figure 4:
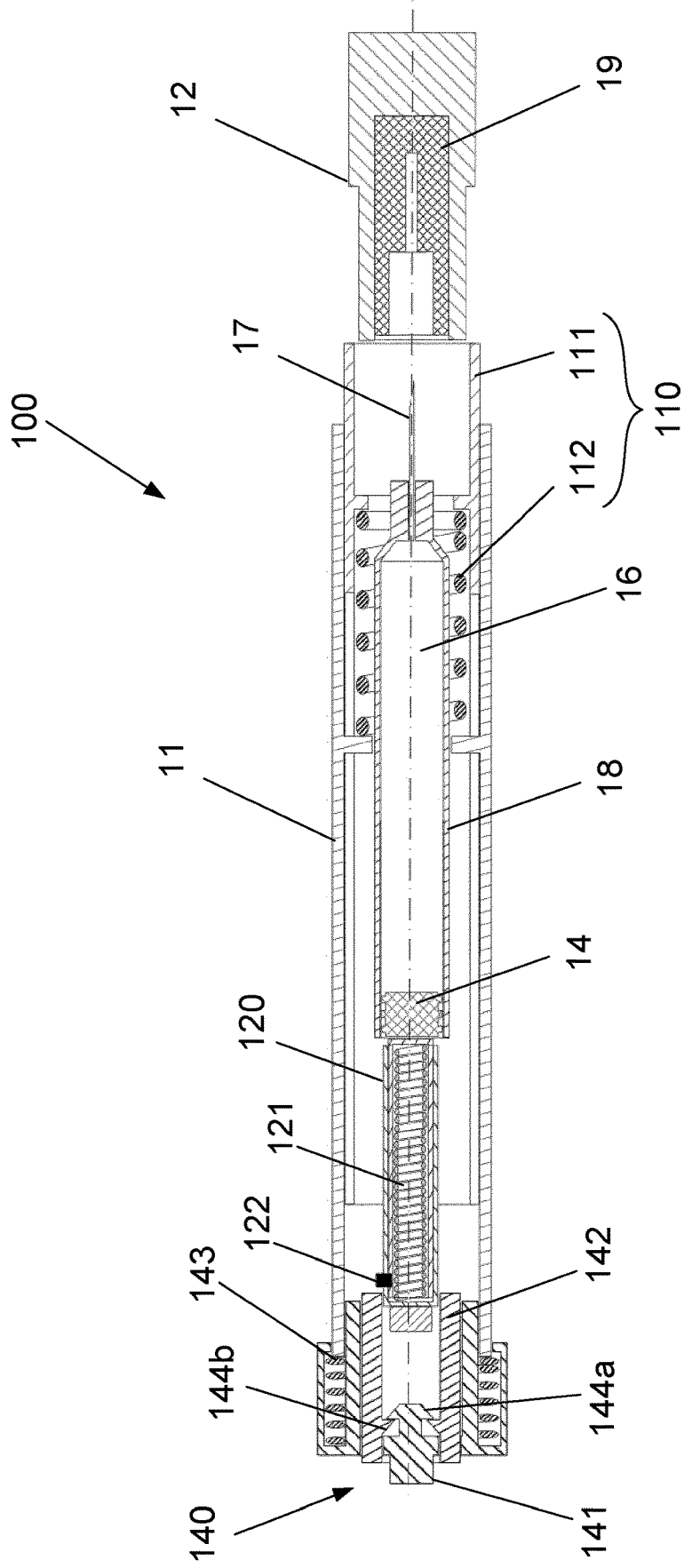
FIG. 4 is a schematic cross-sectional side view of the injection device of FIG. 2.

FIG. 4 shows the first embodiment with the retractable sleeve 111 in the final position. The sleeve spring 112 is expanded and the retractable sleeve 111 extends distally out of the opening at the distal end of the housing 11. The axial movement of the retractable sleeve 111 removes the cap 12 and needle shield 19 from the injection device 100. The retractable sleeve 111 extends beyond the needle 17, which is uncovered by the removal of the cap 12.

The dispense button 140 is shown in a third position, when released after being pressed for the first time. The first part 141 and the second part 142 of the dispense button 140, which are coupled together, are pushed axially away from the housing 11 by the return spring 143. The first part 141 is returned to the initial position, and the second part 142 is also pulled axially in a proximal direction by the coupling elements 144a,144b. The second part 142 protrudes beyond the outer portion of the first part 141 when the dispense button 140 is in the third position and is therefore visible to the user. In some embodiments the second part 142 may be a distinct colour to the first part 141, in order to indicate that the injection device 100 is ready for injection.

The dispense button 140 is engaged with the dispense mechanism 120 when released after being pressed for the first time. The distal end of the second part 142 of the button is arranged to push against the engaging means 122 of the dispense mechanism 120 when the dispense button 140 is in the third position. The engaging means 122 is formed by a sprung element on an outer surface of the dispense mechanism 120 which is initially restrained by the second button and is released when the second part 142 of the dispense button 140 is moved to the third position. The sprung element protrudes from the outer surface of the dispense mechanism 120 when released and engages with the distal end of the second part 142.

Figure 5:
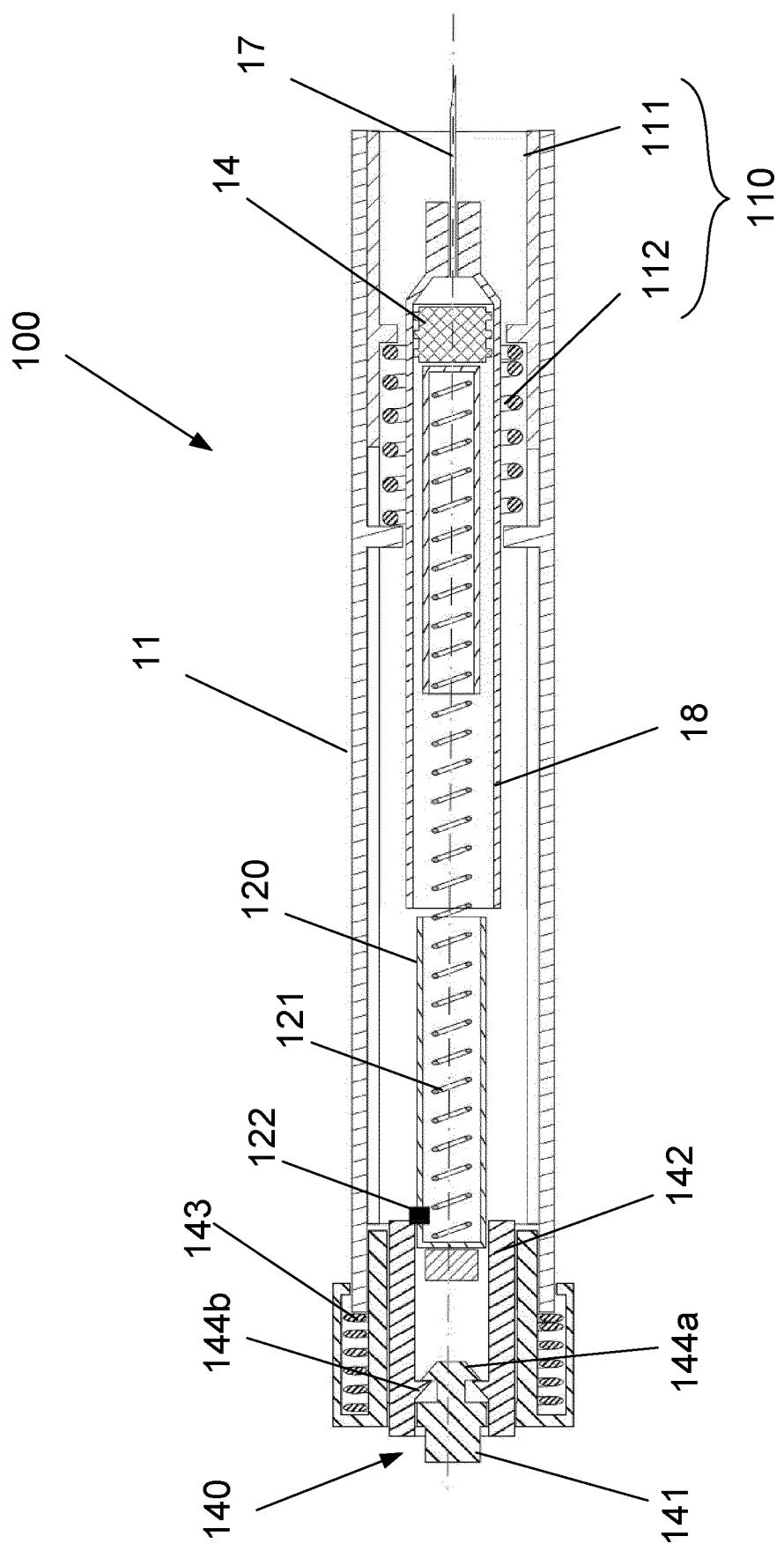
FIG. 5 is a schematic cross-sectional side view of the injection device of FIG. 2.

FIG. 5 shows the dispense mechanism 120 of the first embodiment in a final state, when pressed for a second time. The dispense button 140 is push axially towards the housing 11, such that an axial force is exerted on the engaging means 122 of the dispense mechanism 120. The dispense mechanism 120 is activated by pressing the dispense button 140 for a second time. The driving element 121 is released and expands to drive the rubber stopper 14 through the medicament reservoir. The rubber stopper 14 is moved towards a distal end of the medicament reservoir, such that the liquid medicament 16 is ejected or expelled from the medicament reservoir through the needle 17.

The injection device 100 is held against an injection site on the user before the dispense button 140 is pressed for the second time. The retractable sleeve 111 is pushed axially into the housing 11 on contact with the injection site, allowing the needle 17 to be inserted at the injection site. Once the needle 17 is inserted, the dispense button 140 can be pressed for a second time to activate the dispense mechanism 120 and deliver the liquid medicament 16 through the needle 17. In some embodiments, the retractable sleeve 111 is connected to a locking mechanism, configured to lock the dispense mechanism 120 unless the injection device 100 is being held against the injection site. When the retractable sleeve 111 is pushed into the housing 11, the dispense mechanism 120 is unlocked and can be activated by pushing the dispense button 140 for the second time.

The first embodiment provides an improved injection device 100 which is simple and safe to use. The cap 12 can easily be removed by the cap removal mechanism 110 without requiring the use of a large amount of force, which increases the ease of use and safety of the injection device 100. Furthermore, a single dispense button 140 is used for the activation of both the cap removal mechanism 110 and the dispense mechanism 120, which improves the usability of the device. The second part 142 of the dispense button 140, which may be coloured for contrast with the first part 141 of the dispense button 140, is visible in the third position in order to indicate readiness to the user and further improve the ease of use.

In an alternative embodiment, the dispense button 140 may be brought into engagement with the engaging means 122 using a slotted link mechanism configured to rotate the second part 142 of the dispense button 140 when the second part 142 is moved axially. The slotted link mechanism is formed from an inward protrusion on the second part 142 of the dispense button 140 which is arranged to move through an angled slot on the outer surface of the dispense mechanism 120, to actuate a rotation of the second part 142 when it is moved axially with respect to the dispense mechanism 120. Alternatively, a protrusion on the dispense mechanism 120 may interact in a similar fashion with an angled slot on the second part 142 of the dispense button 140.

The slotted link mechanism translates an axial movement of the second part 142 into a rotational movement. The engaging means 122 is arranged to abut with the distal end of the second part 142 when the second part 142 is rotated into a position of alignment with the engaging means 122.

Figure 6:
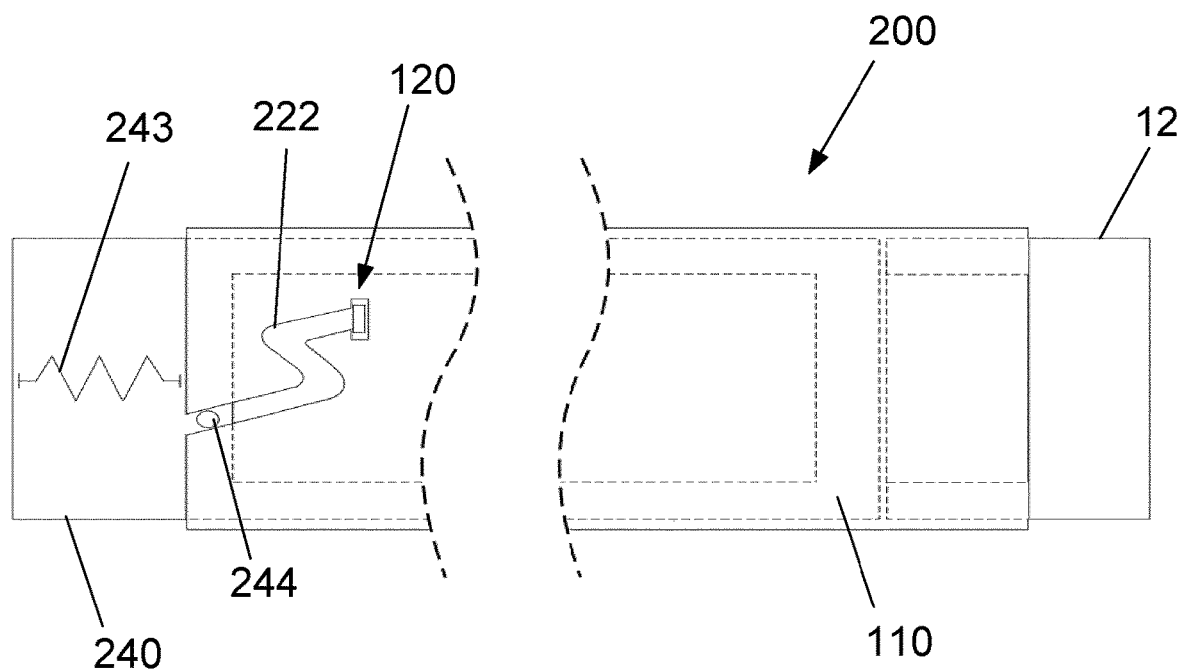
FIG. 6 is a schematic cross-sectional side view of the FIGS. 1A and 1B injection device according to an exemplary embodiment.
Figure 7:
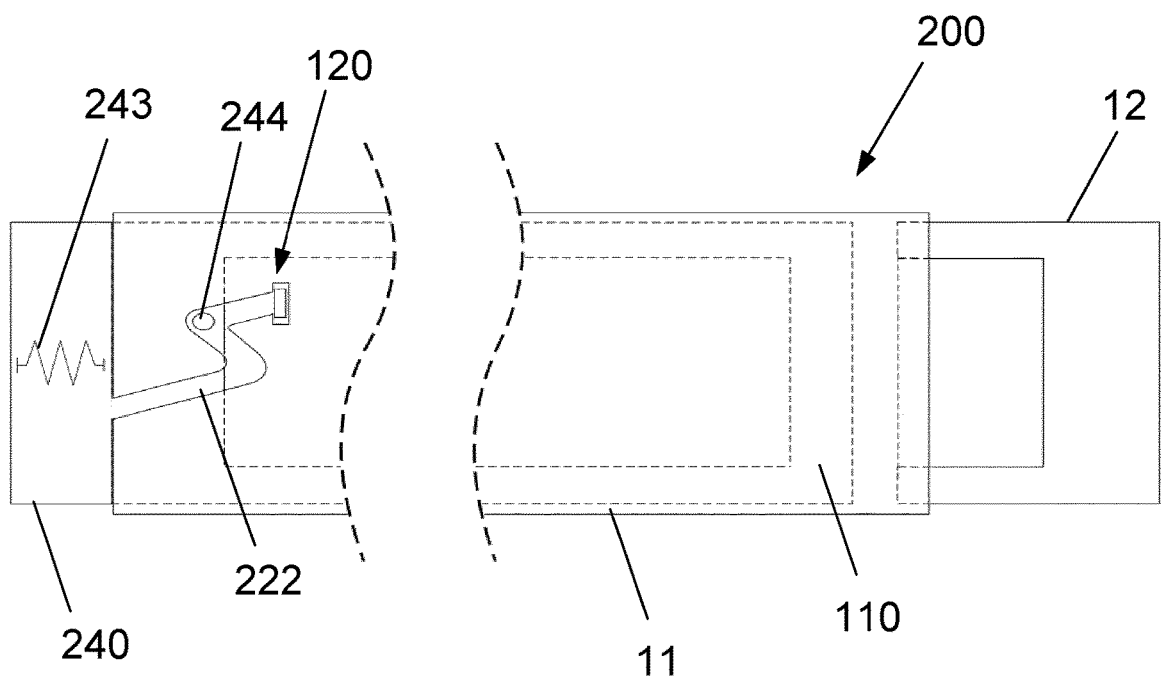
FIG. 7 is a schematic cross-sectional side view of the injection device of FIG. 6.

With respect to FIGS. 6 and 7, an injection device 200 according to a second embodiment is described. Elements not described are substantially the same as those described with respect to the first embodiment.

A dispense button 240 of the second embodiment is formed as a cap which is received in an opening at the proximal end of the housing 11. The dispense button 240 comprises a return spring 243. The return spring 243 exerts an axial force on the dispense button 240 in a proximal direction, so as to bias the dispense button 240 to an initial position. The dispense button 240 further comprises a coupling element 244. The coupling element 244 is coupled to an engaging groove 222 formed in the housing 11.

The engaging groove 222 is formed in a Z-shape. The engaging groove 222 extends longitudinally over a portion of the length of the housing 11 and laterally over a portion of the circumference of the housing 11. The engaging groove 222 comprises a first portion, a second portion and a third portion.

The first portion of the engaging groove 222 extends in a distal direction along a portion of the length of the housing 11, at an angle to the longitudinal axis of the housing 11. The second portion of the engaging groove 222 extends in a proximal direction along a portion of the length of the housing 11, at an angle to the longitudinal axis of the housing 11. The second portion is shorter than the first portion, such that the proximal end of the second portion is further from the proximal end of the housing 11 than the proximal end of the first portion. The third portion of the engaging groove 222 extends in a distal direction along a portion of the length of the housing 11, at an angle to the longitudinal axis of the housing 11. The third portion is longer than the second portion, such that the distal end of the third portion is further from the proximal end of the housing 11 than the distal end of the second portion.

The dispense button 240 is configured to sequentially activate the cap removal mechanism 110 and the dispense mechanism 120. The dispense button 240 activates the cap removal mechanism 110 when pressed a first time and engages with the dispense mechanism 120 when released, such that the dispense mechanism 120 is activated when the dispense button 140 is pressed a second time.

In an initial state, as shown in FIG. 6, the dispense button 240 is in the initial position. The coupling element 244 is located at an initial position at the proximal end of the first portion of the engaging groove 222.

When the dispense button 240 is pressed for the first time, the dispense button 240 is moved axially into the opening at the proximal end of the housing 11. A distal end of the dispense button 240 is pushed against the retractable sleeve 111 of the cap removal mechanism 110. The trigger of the cap removal mechanism 110 is released, as described above. The cap removal mechanism 110 is activated by the dispense button 240 when pressed for the first time.

The coupling element 244 is moved in a distal direction along the first portion of the engaging groove 222. The coupling element 244 is displaced circumferentially by the angle of the engaging groove 222, causing the dispense button 240 to rotate. The axial movement of the coupling element 244 is stopped by contact with the distal end of the first portion of the engaging groove 222. The axial movement of the dispense button 240 is stopped by the coupling element 244.

When the dispense button 240 is released, the return spring 243 urges the dispense button 240 in a proximal direction. The coupling element 244 is moved in a proximal direction along the second portion of the engaging groove 222. The coupling element 244 is further displaced circumferentially by the angle of the engaging groove 222, causing the dispense button 240 to rotate further. The axial movement of the coupling element 244 is stopped by contact with the proximal end of the second portion of the engaging groove 222. The axial movement of the dispense button 240 is stopped by the coupling element 244.

FIG. 7 shows the dispense button 240 in a second state, when the dispense button 240 has been pressed for a first time and released. The coupling element 2444 is located in a second position at the proximal end of the second portion of the engaging groove 222. The coupling element 244 is arranged to engage with the dispense mechanism 120 in the second position.

When the dispense button 240 is pressed for a second time, the dispense button 240 is moved axially into the proximal end of the housing 11. The coupling element 244 is moved in a distal direction along the third portion of the engaging groove 222. The coupling element 244 is further displaced circumferentially by the angle of the engaging groove 222, causing the dispense button 240 to rotate further.

The coupling element 244 is arranged to exert an axial force on the engaging means 122 of the dispense mechanism 120 when moving along the third portion of the engaging groove 222. The driving element 121 is released, as described above. The dispense mechanism 120 is activated by pressing the dispense button 240 for a second time.

The second embodiment provides an improved injection device 200 which is simple and safe to use. The cap 12 can easily be removed by the cap removal mechanism 110 without requiring the use of a large amount of force, which increases the ease of use and safety of the injection device 100. Furthermore, a single dispense button 240 is used for the activation of both the cap removal mechanism 110 and the dispense mechanism 120, which improves the usability of the device.

Figure 8:
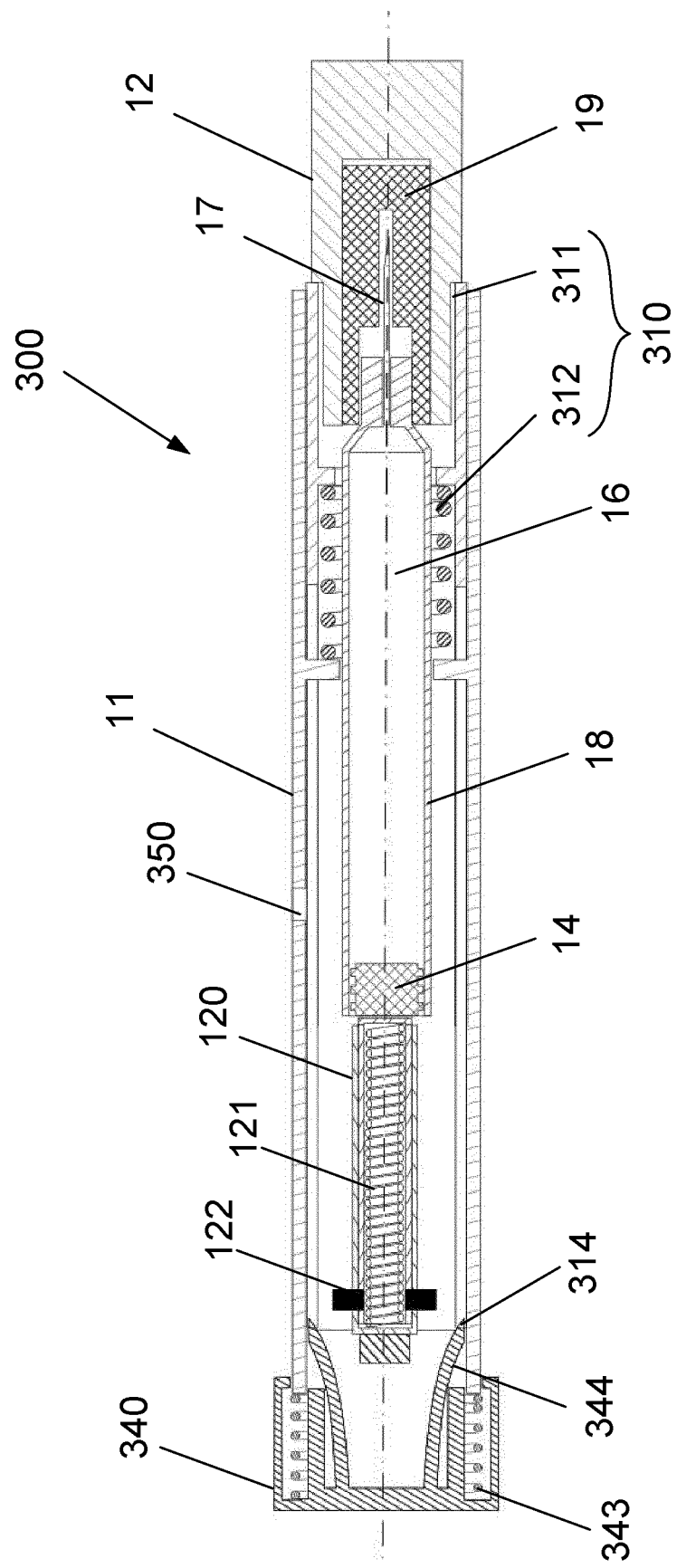
FIG. 8 is a schematic cross-sectional side view of the FIGS. 1A and 1B injection device according to an exemplary embodiment.

With respect to FIG. 8, an injection device 300 according to a third embodiment is described. Elements not described are substantially the same as those described with respect to the first embodiment. A cap removal mechanism 310 of the third embodiment comprises a retractable sleeve 311 and a sleeve spring 312.

A dispense button 340 of the third embodiment is formed as a cap which is disposed over the proximal end of the housing 11, and further comprises a return spring 343 and one or more engaging clips 344. The dispense button 340 has an outer cylindrical wall and an end wall, wherein the outer cylindrical wall is arranged to slideably move over a proximal end of the housing 11. The return spring 343 is disposed between a proximal end of the housing 11 and an inner surface of the end wall, such that the dispense button 340 is pushed axially away from the housing 11 by the return spring 343. An inner cylindrical wall extends from the inner surface of the end wall and is received within the proximal end of the housing 11.

The engaging clips 344 extend into the interior of the housing 11 from the distal side of the dispense button 340. The engaging clips 344 are pre-stressed inwards towards a central longitudinal axis of the housing 11. However, in an initial position, as shown in FIG. 6, the engaging clips 344 curve outwards towards the internal surface of the housing 11. The distal ends of the engaging clips 344 abut with the proximal end of the retractable sleeve 311 and are held in the initial position by an engaging groove 314 in the retractable sleeve 311.

The housing 11 of the third embodiment further comprises a viewing window 350 configured to indicate a status of the injection device 300. The operation of the viewing window 350 is described in more detail below.

Figure 9:
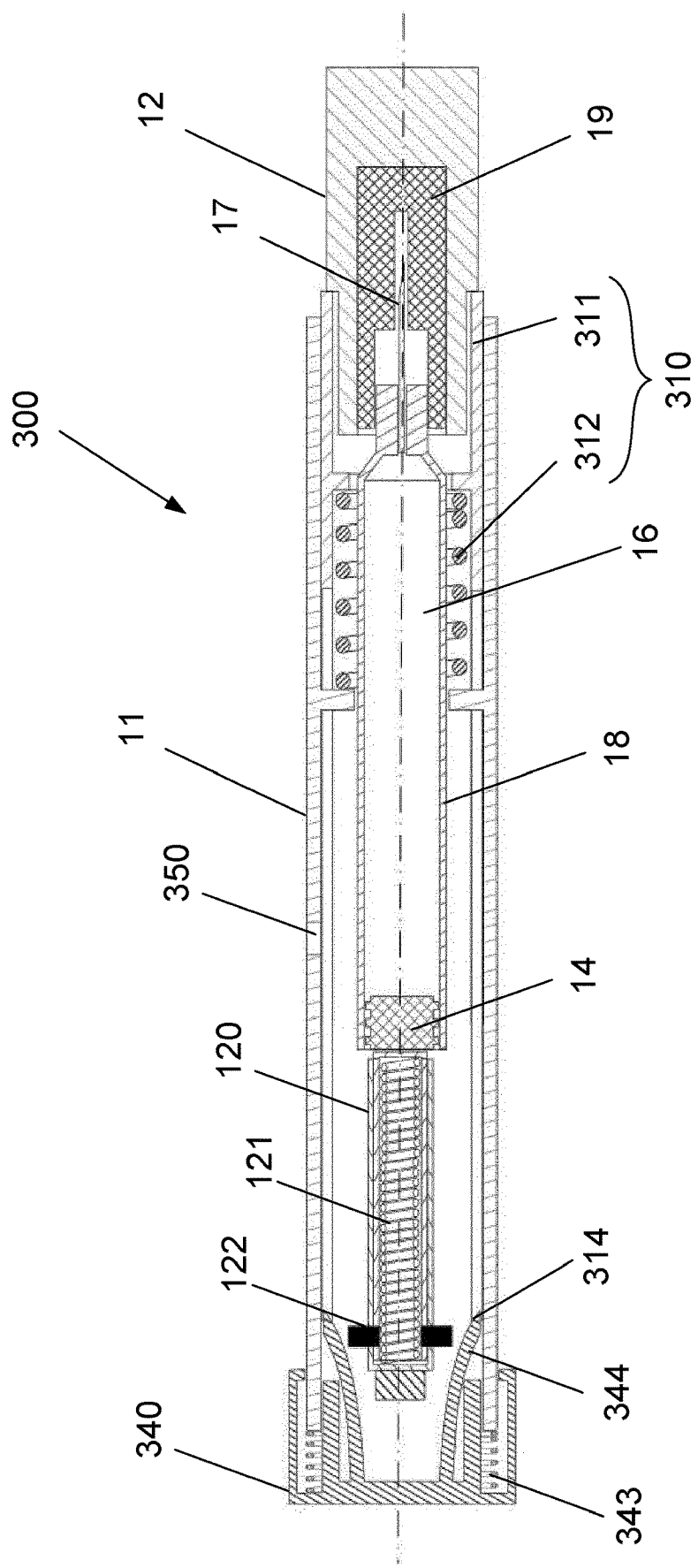
FIG. 9 is a schematic cross-sectional side view of the injection device of FIG. 8.

FIG. 9 shows the dispense button 340 of the third embodiment in a second position, when pressed for a first time. The dispense button 340 is pushed axially in a distal direction towards the housing 11, compressing the return spring 343. The engaging clips 344 exert an axial force on the retractable sleeve 311, which causes the retractable sleeve 311 to move towards a distal end of the housing 11 and releases the trigger of the cap removal mechanism 310. The sleeve spring 112 is released by the trigger and expands to push the retractable sleeve 311 and the cap 12 with the needle shield 19 in a distal direction. The cap removal mechanism 310 is activated by the dispense button 340 when pressed for the first time.

Figure 10:
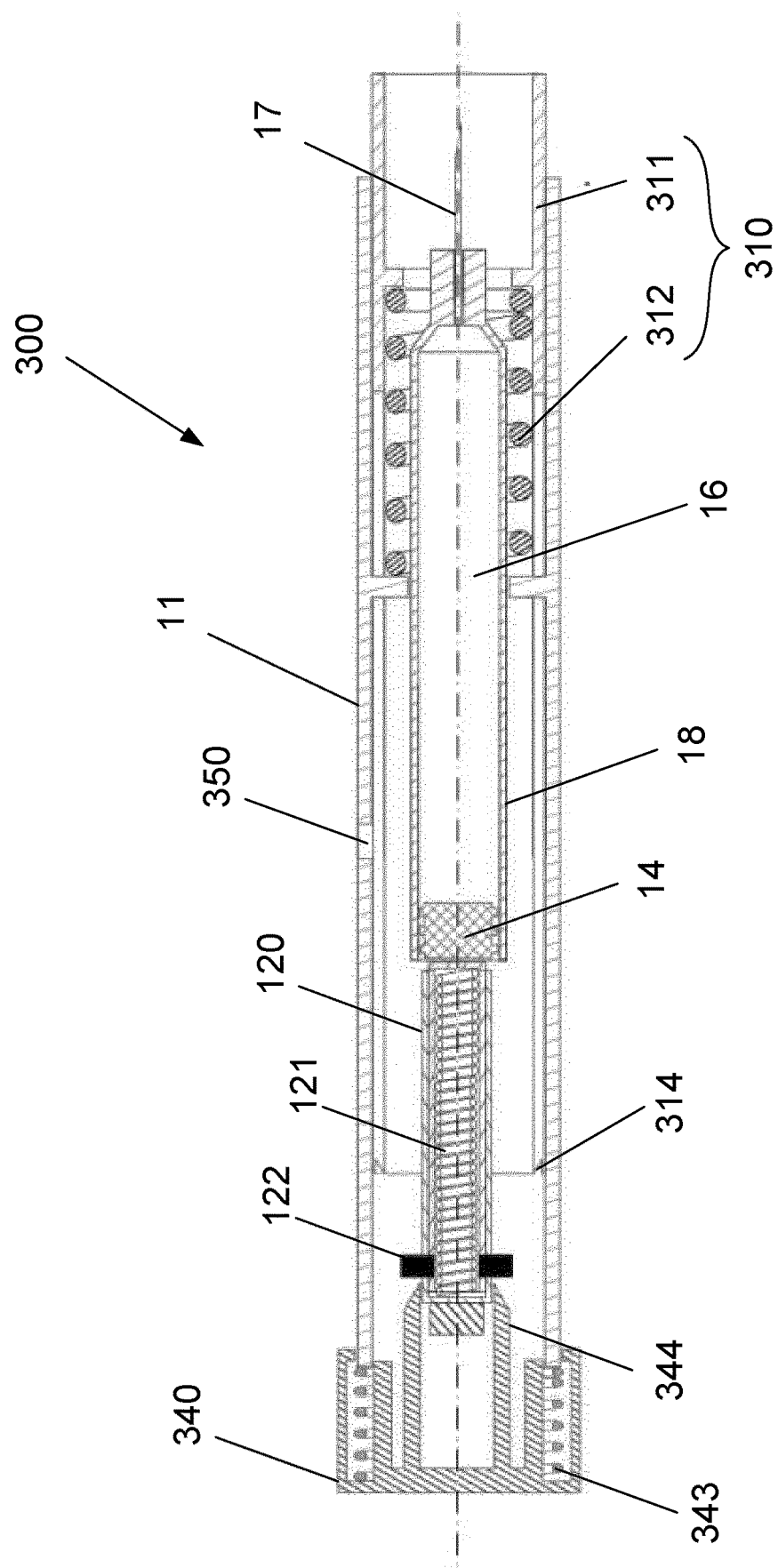
FIG. 10 is a schematic cross-sectional side view of the injection device of FIG. 8.

FIG. 10 shows the third embodiment with the retractable sleeve 311 in the final position. The sleeve spring 112 is expanded and the retractable sleeve 311 extends distally out of the opening at the distal end of the housing 11. The axial movement of the retractable sleeve 311 removes the cap 12 from the injection device 300. The retractable sleeve 311 extends beyond the needle 17, which is uncovered by the removal of the cap 12 and needle shield 19.

The dispense button 340 is shown in a third position, when released after being pressed for the first time. The movement of the retractable sleeve 311 in a distal direction, due to the sleeve spring 112, and the movement of the dispense button 340 in a proximal direction, due to the return spring 343, causes the engaging clips 344 to disengage from the engaging groove 314 of the retractable sleeve 311. The engaging clips 344, which are pre-stressed inwards, bend towards the central longitudinal axis of the housing 11 when released. The distal ends of the engaging clips 344 in the third position abut with an engaging element 122 of the dispense mechanism 120. The engaging element 122 protrudes from an outer surface of the dispense mechanism 120 and a proximal surface of the engaging element 122 abuts with the distal ends of the engaging clips 344 of the dispense button 340.

Figure 11:
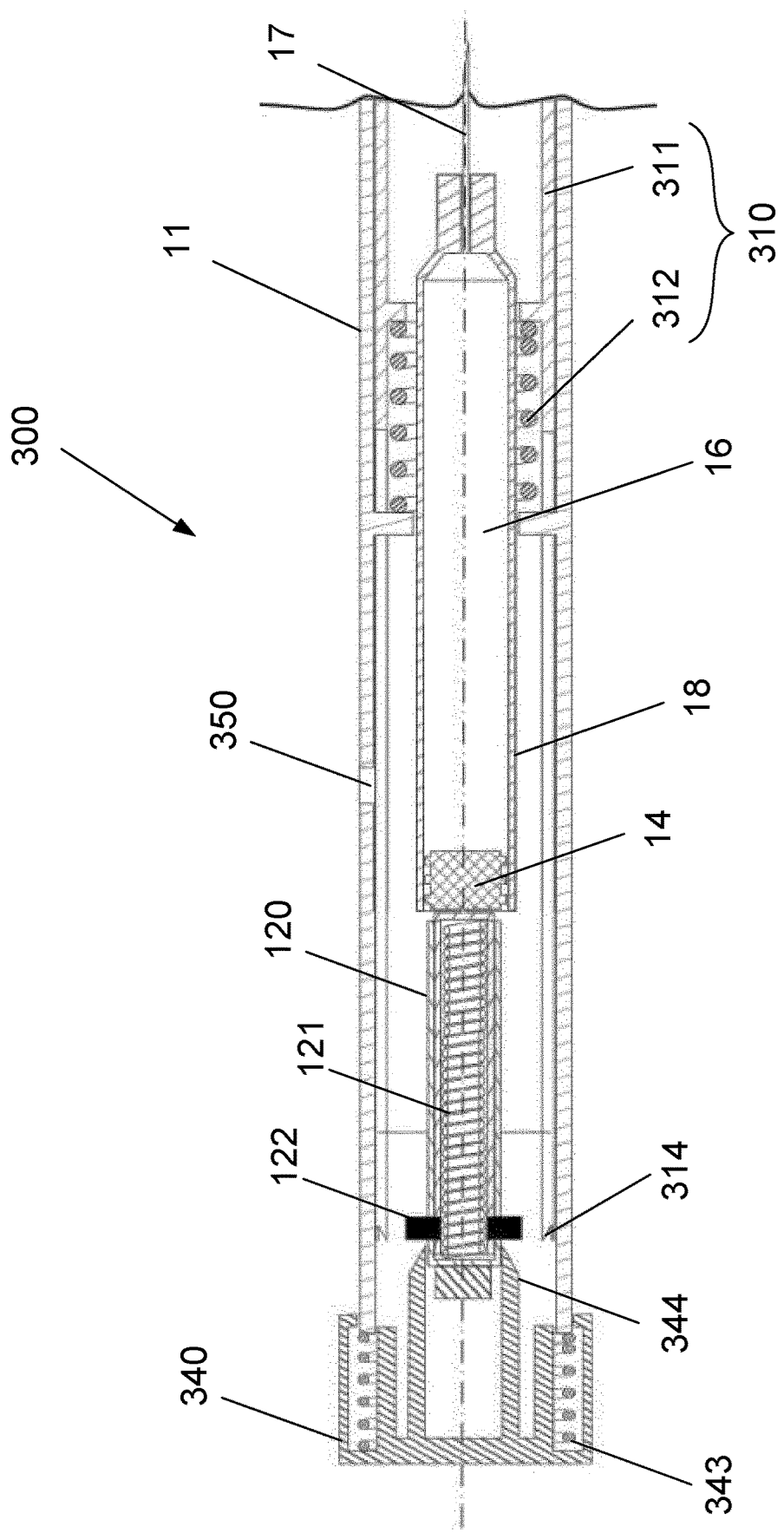
FIG. 11 is a schematic cross-sectional side view of the injection device of FIG. 8.

The injection device 300 is held against an injection site on the user before the dispense button 340 is pressed for the second time, as shown in FIG. 11. The retractable sleeve 311 is pushed axially into the housing 11 on contact with the injection site, allowing the needle 17 to be inserted at the injection site. Once the needle 17 is inserted, the dispense button 340 can be pressed for a second time to activate the dispense mechanism 120 and deliver the liquid medicament 16 through the needle 17. In some embodiments, the retractable sleeve 311 is connected to a locking mechanism, configured to lock the dispense mechanism 120 unless the injection device 300 is being held against the injection site. When the retractable sleeve 311 is pushed into the housing 11, the dispense mechanism 120 is unlocked and can be activated by pushing the dispense button 340 for the second time.

Figure 12:
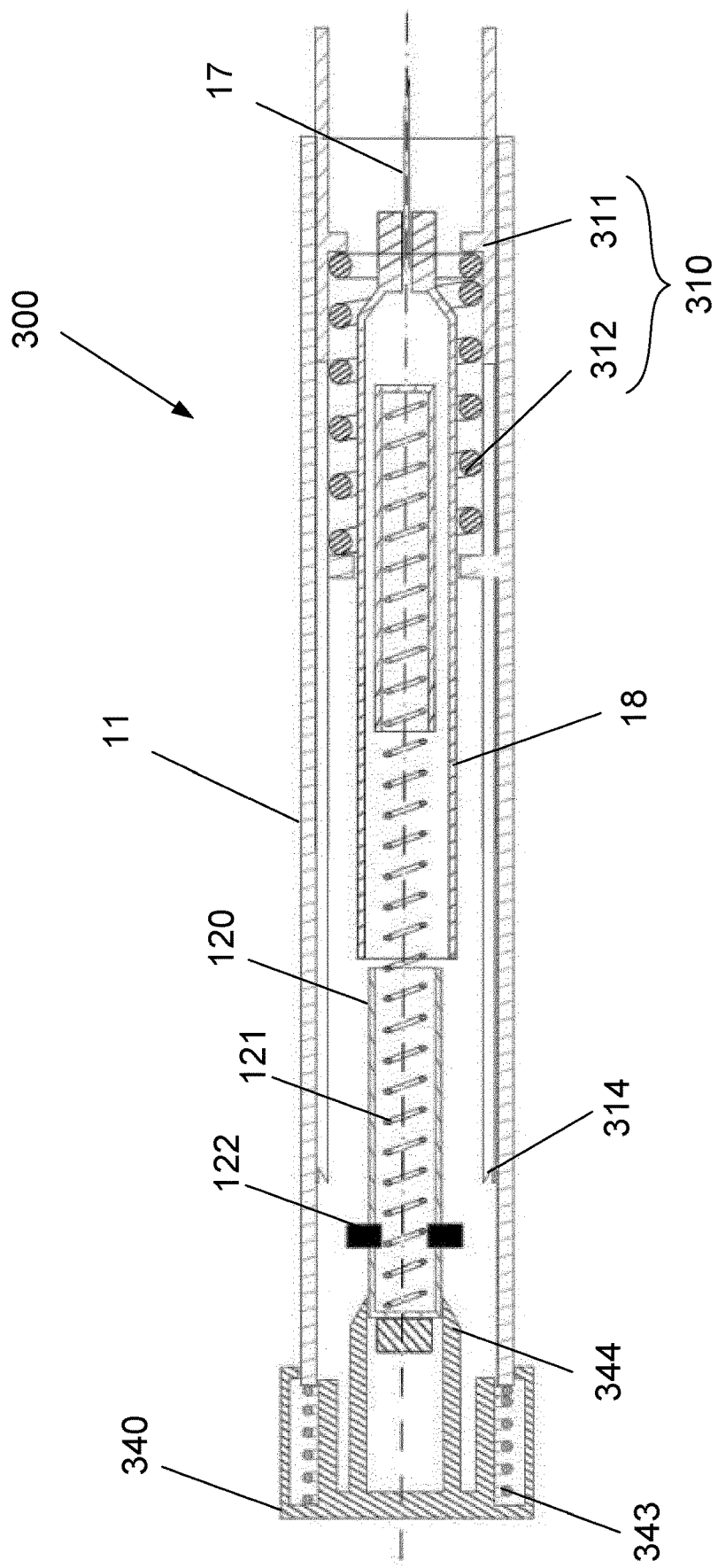
FIG. 12 is a schematic cross-sectional side view of the injection device of FIG. 8.

FIG. 12 shows the third embodiment in a final state, after the dispense button 340 has been pressed and released for a second time. When the dispense button 340 is push axially towards the housing 11 for a second time, an axial force is exerted on the engaging means 122 of the dispense mechanism 120 by the engaging clips 344. The dispense mechanism 120 is activated by pressing the dispense button 340 for a second time. The driving element 121 is released and expands to drive the rubber stopper 14 through the medicament reservoir. The rubber stopper 14 is moved towards a distal end of the medicament reservoir, such that the liquid medicament 16 is ejected or expelled from the medicament reservoir through the needle 17.

In the final state shown in FIG. 12, the dispense button 340 has been released and the needle 17 has been removed from the injection site. The dispense button 340 is pushed away from the housing 11 by the return spring 343 and the retractable sleeve 311 is pushed out of the distal end of the housing 11 by the sleeve spring 112. The retractable sleeve 311 covers the needle 17 in the final state after the injection has been completed. The retractable sleeve 311 is locked in the extended position after the injection has been completed, to prevent injury from the needle.

The third embodiment provides an improved injection device 300 which is simple and safe to use. The cap 12 can easily be removed by the cap removal mechanism 310 without requiring the use of a large amount of force, which increases the ease of use and safety of the device. Furthermore, a single dispense button 340 is used for the activation of both the cap removal mechanism 310 and the dispense mechanism 120, which improves the usability of the device. The viewing window 350 indicates the status of the injection device 300 at each stage of the injection process, which further improves the usability of the device.

Figure 13:
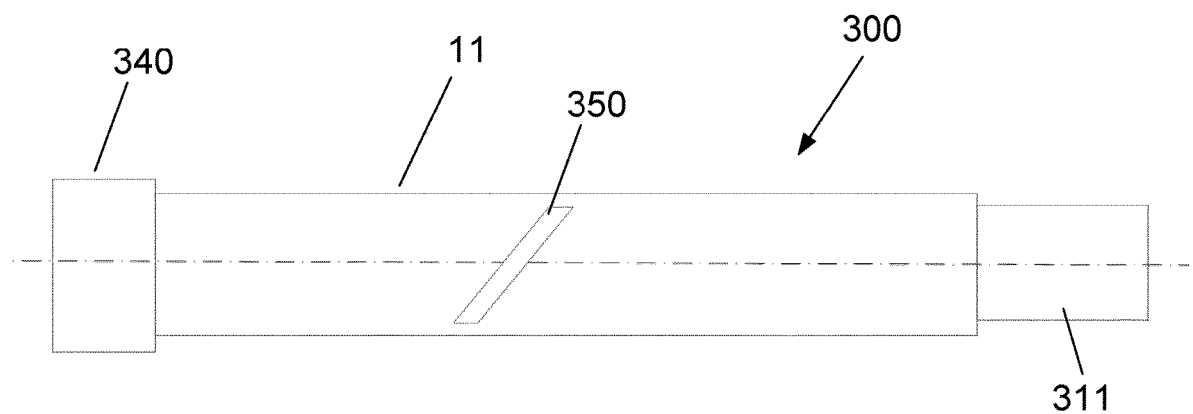
FIG. 13 is a schematic external side view of the injection device of FIG. 8.

FIGS. 13 and 14a to 14d relate to the viewing window 350 of the injection device 300 according to the third embodiment. FIG. 13 shows the position of the viewing window 350 on the outer surface of the housing 11. The viewing window 350 is an opening through the housing 11 which extends diagonally with respect to a longitudinal direction and a circumferential direction on the outer surface. The viewing window 350 is disposed at a location on the housing 11 such that the retractable sleeve 311 is visible through the viewing window 350.

Figure 14A:
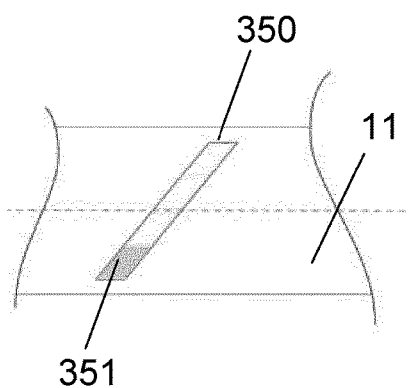
FIG. 14a is a schematic external side view of the injection device of FIG. 8.

FIG. 14a shows the viewing window 350 of the third embodiment in an initial state.

A plurality of status markings 351 are made on an outer surface of the retractable sleeve 311 and an alignment between the viewing window 350 and the retractable sleeve 311 at each stage of the injection process allows the corresponding status marking 351 to be visible through the viewing window 350. The status marking 351 indicate the current state of the injection device 300 by the position of the status indicator within the viewing window 350. In some embodiments, each status indicator may also have a distinct colour, or shape, or a distinct word label. In the initial state, a first status marking 351 corresponding to the initial state is aligned with the viewing window 350 and is visible to the user.

Figure 14B:
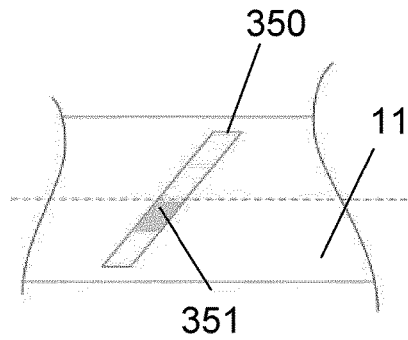
FIG. 14b is a schematic external side view of the injection device of FIG. 8.

FIG. 14b shows the viewing window 350 of the third embodiment in an active state. The activate state corresponds to the third position of the dispense button 340 after being pressed for a first time and released. The retractable sleeve 311 is pushed axially in a distal direction by the sleeve spring 112 in order to remove the cap 12 from the injection device 300.

The retractable sleeve 311 is additionally coupled to the housing 11 with a slotted link mechanism, which is configured to translate the axial movement of the retractable sleeve 311 in the distal direction into a rotation about the longitudinal axis. A protrusion on an inner surface of the housing 11 is engaged with an angled slot in the retractable sleeve 311, so as to exert a turning force on the retractable sleeve 311.

The retractable sleeve 311 is therefore moved axially and rotated with respect to the housing 11, such that the first status marking 351 is no longer aligned with the viewing window 350. A second status marking 351 corresponding to the active state is aligned with the viewing window 350 and is visible to the user.

Figure 14C:
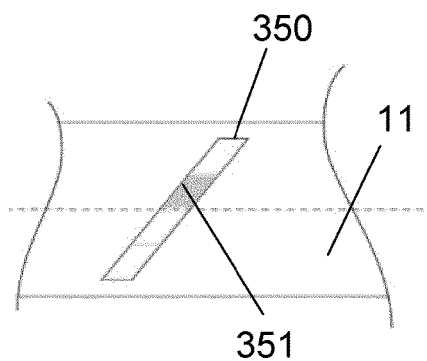
FIG. 14c is a schematic external side view of the injection device of FIG. 8.

FIG. 14c shows the viewing window 350 of the third embodiment in a ready state, when the injection device 300 in the active state is held against the injection site. The retractable sleeve 311 is pushed axially into the housing 11 on contact with the injection site, to allow the needle 17 to be inserted at the injection site. The slotted link mechanism is configured to allow the retractable sleeve 311 to retract axially into the housing 11 without rotation. The retractable sleeve 311 is therefore moved axially with respect to the housing 11, such that the second status marking 351 is no longer aligned with the viewing window 350. The position of the retractable sleeve 311 in the ready state is rotated with respect to the position in the initial state and a third status marking 351 corresponding to the ready state is aligned with the viewing window 350.

Figure 14D:
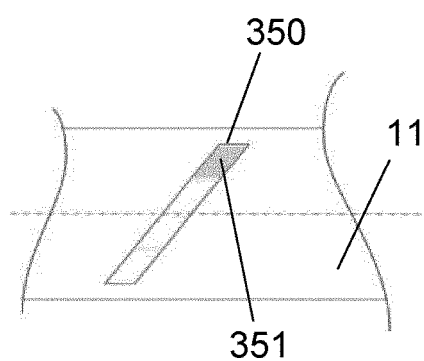
FIG. 14d is a schematic external side view of the injection device of FIG. 8.

FIG. 14d shows the viewing window 350 of the third embodiment in the final state, when the dispense button 340 is pressed and released for the second time and the injection device 300 is removed from the injection site. The retractable sleeve 311 is pushed out of the distal end of the housing 11 by the sleeve spring 112 and a corresponding rotation is imparted to the retractable sleeve 311 by the slotted link mechanism. The retractable sleeve 311 is therefore moved axially and rotated with respect to the housing 11, such that the third status marking 351 is no longer aligned with the viewing window 350.

The position of the retractable sleeve 311 in the final state is rotated with respect to the position in the active state and a fourth status marking 351 corresponding to the final state is aligned with the viewing window 350. Alternatively, the retractable sleeve 311 may be returned to a different axial position after the injection has been completed and the fourth status marking 351 may be axially separated from the third status marking 351. The retractable sleeve is locked in position after the injection has been completed.

The third embodiment provides a viewing window 350 which is configured to indicate the status of the injection device 300 at each stage of the injection process, which further improves the usability of the device. In an alternative embodiment, the arrangement of the slotted link mechanism may be reversed, such that the retractable sleeve 311 is caused to rotate when it is moved axially in a proximal direction.

Although a few embodiments have been shown and described, it will be appreciated by those skilled in the art that changes may be made in these embodiments without departing from the disclosure, the scope of which is defined in the appended claims. Various components of different embodiments may be combined where the principles underlying the embodiments are compatible. For example, the viewing window described with respect to the third embodiment may be implemented as part of the injection device according to the first embodiment.

In an alternate embodiment, a viewing window may be formed as an aperture in an outer cylindrical wall of the dispense button, which fits over the proximal end of the housing. A plurality of status markings are made on the outer surface of the housing and an alignment between the viewing window and the housing determines which of the status markings is visible through the viewing window. The alignment between the viewing window and the housing is determined by the relative position of the dispense button and the housing. The axial position of the dispense button may be varied as the button is pressed for the first and the second time, and the dispense button may additionally be caused to rotate relative to the house by means of a slotted link mechanism, as described above.

The housing, cap and dispense button of any embodiment may have a square, circular or triangular cross-section, or any other suitable shape. The cap may be formed to receive the distal end of the housing within the interior of the cap, such that an inner surface of the cap abuts an outer surface of the housing to retain the cap thereon. Alternatively, the cap may fit within the housing, but around the outside of the retractable sleeve. The needle shield may be a flexible shield formed from rubber, or an artificial rubber-like material, or may be a rigid needle shield formed from, for example, a rigid plastic material.

The cap removal mechanism may be any other such mechanism which can be triggered by a button press, for example, the first press of the dispense button may trigger a compressed gas release or activate an electric motor to remove the cap. The cap removal mechanism may include any retractable component, such as one or more retractable arms, which can be driven axially in a distal direction to remove the cap.

The dispense mechanism may also include any suitable dispense mechanism. For example, the second press of the dispense button may trigger a compressed gas release or activate an electric motor to drive the rubber stopper through the medicament reservoir. The syringe and dispense mechanism may be a needle-less arrangement, which is configured to squirt a fine jet of liquid medicament at sufficient pressure to penetrate the skin at the injection site. The dispense mechanism may include a compressed gas source to expel the liquid medicament at a high pressure. The dispense mechanism may be activated automatically upon pushing the retractable sleeve completely within the housing when the injection device is in an active state, that is, by pressing the device against the injection site.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids.

Optionally, one or more amino acids occurring in the naturally occurring peptide may have been deleted and/or replaced by other amino acids, including non-codable amino acids, or amino acids, including non-codable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that can be useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof

What is claimed is:

1. An auto-injector device comprising:
a cap removal mechanism comprising a retractable component which is slidably mounted within a housing of the auto-injector device, and a cap-removal actuator configured to push the retractable component out of the housing to remove a cap from the auto-injector device;
a dispense mechanism comprising a driving element configured to expel a medicament from the auto-injector device; and
a dispense button configured to activate the cap removal mechanism when the dispense button is pressed a first time, to engage with the dispense mechanism when released, and to cause the dispense mechanism to expel the medicament from the auto-injector device, by the engagement, when the dispense button is pressed a second time,
wherein the dispense mechanism comprises an engaging element configured to engage with the dispense button when the dispense button has been pressed for the first time and released.

2. The auto-injector device of claim 1, wherein the cap-removal actuator comprises a cap-removal spring.

3. The auto-injector device of claim 1, wherein the dispense mechanism comprises locking means configured to prevent activation of the dispense mechanism when locked; and
wherein the retractable component is configured to unlock the locking means when the retractable component is pushed within the housing of the auto-injector device.

4. The auto-injector device of claim 1, wherein the retractable component is in the form of a retractable sleeve.

5. The auto-injector device of claim 1, wherein the dispense button comprises a first part and a second part, and wherein the first part is configured to couple with the second part when the dispense button has been pressed the first time, and to retract with the second part when the dispense button has been released.

6. The auto-injector device of claim 5, wherein the second part of the dispense button is a different colour to the first part of the dispense button.

7. The auto-injector device of claim 5, wherein the second part of the dispense button when retracted by the first part is arranged to engage with the engaging element of the dispense mechanism and is configured to activate the dispense mechanism when the dispense button is pressed the second time.

8. The auto-injector device of claim 7, wherein the engaging element is restrained in a disengaged position by the second part of the dispense button, and is configured to move into an engaging position when the dispense button is released;
wherein the engaging element is arranged to engage with the second part in the engaging position.

9. The auto-injector device of claim 1, wherein the dispense button comprises a spring element which is retained in a disengaged position by the cap removal mechanism and, when the cap removal mechanism is activated, is configured to move into an engaging position;
wherein the spring element is arranged to engage with the dispense mechanism in the engaging position.

10. The auto-injector device of claim 1, further comprising an active status marking which is uncovered when the dispense button is pressed for the first time and released.

11. The auto-injector device of claim 10, further comprising a viewing window which is moved into alignment with the active status marking when the dispense button is pressed for a first time and released.

12. The auto-injector device of claim 11, further comprising an initial status marking and a final status marking; wherein the viewing window is aligned with the initial status marking before the dispense button is pressed, and aligned with the final status marking when the dispense button is pressed for a second time.

13. The auto-injector device of claim 1, further comprising the medicament which is retained in a medicament reservoir and is arranged to be expelled from the medicament reservoir by the dispense mechanism.

14. A method of operating an auto-injector device, comprising:
activating the cap removal mechanism of the auto-injector device of claim 1 in response to a received input; and
activating the dispense mechanism of the auto-injector device in response to the received input, if the input is received a second time.

15. The auto-injector device of claim 1, wherein the driving element is a mechanical energy source.

16. The auto-injector device of claim 1, wherein the engaging element is a sprung element configured to protrude from an outer surface of the dispense mechanism.

17. The auto-injector device of claim 1, wherein activating the dispense mechanism comprises releasing the driving element such that the driving element drives a rubber stopper through a medicament reservoir containing the medicament to expel the medicament.

18. The auto-injector device of claim 1, further comprising a needle for expelling the medicament.

19. An auto-injector device comprising:
a cap removal mechanism comprising a retractable component which is slidably mounted within a housing of the auto-injector device, and a cap-removal actuator configured to push the retractable component out of the housing to remove a cap from the auto-injector device;
a dispense mechanism comprising a driving element configured to expel a medicament from the auto-injector device; and
a dispense button configured to activate the cap removal mechanism when pressed a first time, to engage with the dispense mechanism when released, and to activate the dispense mechanism when pressed a second time,
wherein the dispense mechanism comprises an engaging element configured to engage with the dispense button when the dispense button has been pressed for the first time and released,
wherein the dispense button comprises a first part and a second part, and wherein the first part is configured to couple with the second part when the dispense button has been pressed the first time, and to retract with the second part when released, wherein the second part of the dispense button when retracted by the first part is arranged to engage with the engaging element of the dispense mechanism and is configured to activate the dispense mechanism when the dispense button is pressed the second time,
wherein the engaging element is restrained in a disengaged position by the second part of the dispense button, and is configured to move into an engaging position when the dispense button is released, and wherein the engaging element is arranged to engage with the second part in the engaging position.

20. An auto-injector device comprising:
a cap removal mechanism comprising a retractable component which is slidably mounted within a housing of the auto-injector device, and a cap-removal actuator configured to push the retractable component out of the housing to remove a cap from the auto-injector device;

a dispense mechanism comprising a driving element configured to expel a medicament from the auto-injector device; and a dispense button configured to activate the cap removal mechanism when pressed a first time, to engage with the dispense mechanism when released, and to activate the dispense mechanism when pressed a second time, wherein the dispense mechanism comprises an engaging element configured to engage with the dispense button when the dispense button has been pressed for the first time and released, wherein the dispense button comprises a spring element which is retained in a disengaged position by the cap removal mechanism and, when the cap removal mechanism is activated, is configured to move into an engaging position, and wherein the spring element is arranged to engage with the dispense mechanism in the engaging position.

\* \* \* \* \*